(12) United States Patent
Shirley

(10) Patent No.: US 7,041,305 B2
(45) Date of Patent: May 9, 2006

(54) STABLE WATER IN OIL AMINOPHYLLINE EMULSIONS

(75) Inventor: Kenneth Shirley, Evanston, WY (US)

(73) Assignee: Western Holdings, LLC, Casper, WY (US)

(*) Notice: Subject to any disclaimer, the term of this patent is extended or adjusted under 35 U.S.C. 154(b) by 169 days.

(21) Appl. No.: 10/230,857

(22) Filed: Aug. 29, 2002

(65) Prior Publication Data

US 2003/0050318 A1   Mar. 13, 2003

Related U.S. Application Data

(60) Provisional application No. 60/328,907, filed on Oct. 12, 2001, provisional application No. 60/317,905, filed on Sep. 7, 2001.

(51) Int. Cl.
*A61K 6/00* (2006.01)
*A61K 31/52* (2006.01)

(52) U.S. Cl. ............... 424/401; 514/263; 514/938

(58) Field of Classification Search ........... 514/263, 514/938, 936; 424/401
See application file for complete search history.

(56) References Cited

U.S. PATENT DOCUMENTS

| 4,073,907 A | 2/1978 | Guzek | |
|---|---|---|---|
| 4,584,294 A * | 4/1986 | Ruyle | 514/150 |
| 5,422,352 A * | 6/1995 | Astrup | 514/263.31 |
| 5,554,359 A * | 9/1996 | Fuller | 424/59 |
| 5,654,337 A * | 8/1997 | Roentsch et al. | 514/570 |
| 5,705,170 A * | 1/1998 | Kong et al. | 424/401 |
| 5,905,091 A * | 5/1999 | Fuller | 514/573 |
| 5,942,545 A * | 8/1999 | Samour et al. | 514/573 |
| 6,197,830 B1 * | 3/2001 | Frome | 514/654 |
| 6,294,186 B1 * | 9/2001 | Beerse et al. | 424/405 |
| 6,387,957 B1 | 5/2002 | Frome | |
| 6,391,869 B1 * | 5/2002 | Parks et al. | 514/211.07 |
| 6,395,736 B1 * | 5/2002 | Parks et al. | 514/248 |
| 6,627,632 B1 * | 9/2003 | Parks et al. | 514/252.19 |
| 2002/0111495 A1 * | 8/2002 | Magee et al. | 546/291 |
| 2002/0193831 A1 * | 12/2002 | Smith, III | 607/2 |

FOREIGN PATENT DOCUMENTS

| DE | 23 64 373 | 7/1975 |
|---|---|---|
| EP | 0 147 282 | 7/1985 |
| EP | 0 700 678 A1 | 3/1996 |
| FR | 2 777 180 | 10/1999 |
| FR | 2 797 765 | 3/2001 |
| IT | 1304342 | 3/2001 |
| WO | WO 98/00101 | 1/1998 |

OTHER PUBLICATIONS

Dickinson et al., "Aminophylline For Cellulite Removal," The Annals of Pharmacology., 30(3):292-293 (1996).

* cited by examiner

*Primary Examiner*—Vickie Kim
*Assistant Examiner*—Henrietta Dandy
(74) *Attorney, Agent, or Firm*—Morriss O'Bryant Compagni, PC

(57) ABSTRACT

A water in oil emulsion system and a process for preparing such a emulsion has been provided for topically applying aminophylline for reducing cellulite conditions.

22 Claims, No Drawings

STABLE WATER IN OIL AMINOPHYLLINE EMULSIONS

CROSS REFERENCE TO RELATED APPLICATIONS

This Application claims the benefit of the following provisional applications, Ser. No. 60/317,905 filed Sept. 7, 2001 and U.S. Ser. No. 60/328,907 filed Oct. 12, 2001.

FIELD OF THE INVENTION

This invention relates to health care and cosmetics and, more particularly, to novel systems and methods for creating aminophylline products for cellulite reduction.

BACKGROUND

Aminophylline is an effective agent, when properly administered, for reducing cellulite. In fact, aminophylline helps reduce cellulite when applied topically to appropriate areas of the human body. Unfortunately, aminophylline has only been marginally effective as a commercial agent due to the difficulties in applying it by means of a topical formulation. Providing an effective delivery system whereby the aminophylline can be stored in stable form and topically applied to the skin so that aminophylline can be transported to the affected areas has been the problem. Mechanisms have not been available to formulate stable compounds of aminophylline in useful carriers. For example, separation of constituents and particularly the aminophylline from the composition has been a perennial problem. In fact, there have been various attempts to provide stable injectable aqueous solutions of aminophylline where the aminophylline does not crystallize out of solution such as disclosed in U.S. Pat. No. 4,073,907. However, these procedures have proven costly.

Compounds such as aminophylline that might be operative transdermally to a targeted area have been particularly problematic, needing a non-separable, shelf-stable topical composition for commercial application. For example, dissolving aminophylline in a solution, such as water, and mixing it with a carrier, has been difficult since the aminophylline does not stay dissolved in the solution. Thus compounding, composition, storage, application and delivery of aminophylline are all important issues for the commercial application of this material.

SUMMARY OF INVENTION

In accordance with this invention, a water in oil emulsion system has been provided for topically applying aminophylline for reducing cellulite conditions in human subjects. The aminophylline is stable in the emulsion system of this invention and does not precipitate out or undergo undesirable crystal growth in this system. In accordance with the features of this invention, the aminophylline is maintained in the system in the emulsion and any undesirable crystal growth is prevented. In this manner, topical compositions are obtained whereby aminophylline remains in solution in the emulsions. Also the emulsion of this invention allow the aminophylline to be topically applied to the skin so that it can be transdermally transported through the skin to effectively reduce cellulite conditions in people afflicted with these problems.

DETAILED DESCRIPTION OF THE INVENTION

In accordance with this invention, a water in oil emulsion for topically applying aminophylline to reduce cellulite is provided. This water in oil emulsion comprises a water phase dispersed as a plurality of discreet micellular particles in a continuous oil phase with the water phase containing the aminophylline and a pseudoplastic or thixotropic agent and the oil phase containing lecithin dissolved in a cosmetically acceptable hydrocarbon oil. The lecithin in this composition acts as a carrier for the aminophylline so that it can be transported transdermally through the skin upon topical application of this emulsion to the skin of a human subject. The emulsion of this invention provides a system wherein the aminophylline present in solution in a water phase is maintained in the aqueous solution without the danger of precipitating or resolidifying. In this way, an inseparable, shelf-stable, flowable, topical preparation is provided for applying aminophylline topically to skin.

In accordance with this invention, a process for preparing such a an emulsion is provided. This process for preparing this water in oil emulsion produces a system whereby aminophylline is maintained in a stable condition in solution in the water phase of the emulsion without a danger of solidifying. This process is carried out by providing an oil solution formed by dissolving the lecithin carrier in the hydrocarbon oil. An aqueous solution is prepared by first dissolving a pseudoplastic or thixotropic agent in an aqueous medium and then dissolving aminophylline in this aqueous medium. When the aminophylline is dissolved in the aqueous solution, the aqueous solution should be added to the oil solution while the aminophylline remains in solution. In order to carry out the mixing of the oil and water solutions while the aminophylline remains dissolved in the aqueous solution, it is important to carry out this mixing step before the aminophylline starts to separate from the aqueous solution. In order to maintain the aminophylline in solution, this mixing of the oil and water solutions should be done very quickly since aminophylline will not remain dissolved in the aqueous solution for very long.

For example, one can incorporate into the topical preparations described above additives such as preservatives, coloring agents, perfumes and the like which are recognized as being conventional in the art of pharmaceutical compounding. In addition, it is contemplated to incorporate into the topical preparations herein described one or a mixture of conventional antioxidants such as, for example, N-methyl-α-tocopherolamine, tocopherols, butylated hydroxyanisole, butylated hydroxy-toluene, ethoxyquin and the like.

Aminophylline, which is the active ingredient in the composition of this invention, is present in amount which is effective for use in topically treating cellulite conditions. Topical compositions of this invention can be conventionally prepared as ointment, tinctures, gels, lotions, creams, serums and pastes. The aminophylline in these compositions can be in any amount which when applied topically will cause a reduction of the cellulite in human subjects. However, the amount of aminophylline and the frequency of administration of topical application will depend to a large extent on the severity of the cellulite condition in the individual and the ability of the individual with this problem to respond. In general, emulsions of this invention contain from about 0.1% by weight to about 5% by weight of aminophylline based upon the weight of the emulsions.

In accordance with the preferred embodiment of this invention, the aminophylline in the water phase contains ethylenediamine which is also dissolved in the water phase. The ethylenediamine is an aid in maintaining the aminophylline in solution. Therefore, in accordance with this preferred embodiment, ethylenediamine is incorporated into the aqueous phase in the solution containing aminophylline. Generally, the ethylenediamine incorporated in the aqueous medium to provide concentration of from about 0.001% to about 2.5% by weight of the weight of the emulsion thus produced.

In accordance with this invention, it has been found that in order to provide aminophylline in the aqueous solution so as to produce the water in oil emulsion with the aminophylline trapped in the aqueous solution, it is necessary to incorporate a pseudoplastic or thixotropic agent in said aqueous solution prior to the addition of the aminophylline. It has been found that the results of this invention of trapping aminophylline within the emulsion is achieved through the use of thixotropic or pseudotropic agents in the aqueous phase of this emulsion. In fact, in accordance with this invention, any thixotropic or pseudoplastic agent can be utilized. However, best results are achieved through the use of pseudoplastic agents and in particular the carbomers. Generally, these agents are incorporated into the aqueous phase prior to the addition of aminophylline in an amount to provide the emulsion with from about 0.003% to about 2% by weight of this agent, based upon the weight of emulsion thus produced. The preferred agent is the pseudoplastic agent and in particular the carbomers.

As set forth above, carbomers are the preferred agents for maintaining the homogenous dispersion of aminophylline trapped within the water phase of a water/oil emulsion. A carbomer is water soluble polyacrylate which is a homopolymer of acrylic acid which can be an allyl ether of pentaerytheritol, sucrose or propylene. These high molecular crossed linked polymers of acrylic acid contain about 56% to 68% of carboxylic acid groups. Particularly, the preferred carbomer for use in this invention is Carbomer 940 which has a viscosity of 40,000 to 60,000 cps in a 0.59% aqueous solution.

In accordance with a preferred embodiment of this invention, the water phase along with the thixotropic or pseudoplastic agent, contains glycerin. Generally, if glycerin is used, glycerin is present in an amount of from about 1% to about 20% by weight based upon the weight of emulsion thus produced. Glycerin is present along with the thixotropic or pseudoplastic agent in the aqueous solution. In accordance with a preferred embodiment of this invention, both the carbomer and the glycerin are present in the aqueous solution before it is mixed with the aminophylline and ethylene diamine. The carbomer and the glycerin provide increased thickening properties to allow the aminophylline to be maintained in the solution of the aqueous phase.

The lecithin carrier for aminophylline is contained in the oil phase. The lecithin carrier when it is topically applied to the skin can provide a means for transporting the aminophylline into the skin so that it is effective in treating the cellulite condition. Generally, the lecithin is present in the composition in the amount of from about 2% to about 80% by weight, based upon the weight of emulsion thus produced. In preparing the composition lecithin granules are dissolved in the oil phase which is formed from a cosmetically acceptable organic oil which is a solvent for lecithin. Any conventional cosmetically acceptable water insoluble organic oil which is a solvent for lecithin can be utilized to form the oil phase in which the aqueous micelles of aminophylline are dispersed. Among the water insoluble organic oils which are solvents for lecithin are included those listed by Luisi, et al. in Table 5 on page 365 of *Colloid Polym Science,* 268:356–374 (1990). Among the preferred organic oils are the hydrocarbon oils with octyl palmitate being especially preferred. The oil phase is prepared by dissolving the lecithin granules in the solvent. Generally, the solvent such as octyl palmitate is present in an amount of from about 1% to 80% by weight based upon the weight of the emulsion.

If desired, the topical compositions of this invention can contain the common excipients used in these compositions. For example, the aqueous phase prior to the addition of aminophylline and ethylenediame may contain conventional pharmaceutical excipients such as preservatives which include DMDM hydantoin and iodopropynyl butyl carbamate, etc. In addition, the oil soluble phase can, if desired, contain various fragrances, coloring agents, preservatives and anti-oxidants which are common in preparing the topical compositions. Once the emulsion is formed, ethanol can be added to lower the viscosity of the resulting emulsion to a desired range depending upon whether one wishes to prepare a gel, cream, ointment, lotion, paste, or serum.

In producing these topical products, the use or non-use of ethanol is dependent upon the viscosity of the final type of topical product desired. In this respect, the mixture of oil and water in the composition can be varied to increase or decrease viscosity so as to produce the type of topical product desired. Generally, water is present in an amount of from about 2% by weight to 96.5% by weight depending upon the type of final composition desired. In accordance with and based upon the various types of topical products desired the preferred percentages (w/w) of the constituents in these compositions are as follows:

|  | Preferred Range: | |
| --- | --- | --- |
|  | Gel, Serum, Paste | Lotion and Cream |
| Octyl Palmitate | 10–20% | 3.3–13.3% |
| Lecithin | 20–40% | 6.6–26.6% |
| Deionized Water | 40–70% | 60–90% |
| Carbomer | 0.01–0.4% | 0.05–1% |
| Glycerin | 2–10% | 2–10% |
| Aminophylline | 0.5–2 | 0.5–2% |
| Ethylenediamine | 0.125–0.5% | 0.125–0.5% |
| Ethanol | q.s. | q.s. |

In preparing the emulsions of this invention, a first solution is provided by dissolving granular lecithin in the cosmetically acceptable oily organic solvent. Again, as set forth above, the preferred solvents are the oily hydrocarbon solvents, particularly octyl palmitate. The lecithin granuals are dissolved with agitation in octyl palmitate to produce a homogenous solution and air bubbles are removed by any suitable method. The second solution is prepared by dissolving the thixotropic or pseudoplastic agent in the water with moderate agitation until fully hydrated. In forming this aqueous solution, the preferred agent is a pseudoplastic agent, particularly the carbomers such as Carbomer 940. In addition, if desired, after the carbomer has been added and if desired, glycerin has been added, the water soluble preservatives such as those mentioned hereinbefore can be added to the aqueous solution. After these ingredients are added to the aqueous solution, aminophylline may be then added to the solution and agitated until clear. If desired, ethylenediamine which enhances the solubility of aminophylline in the aqueous solution can be added together with the aminophylline.

After mixing the aminophylline into the aqueous solution so that the aminophylline dissolves in the aqueous solution, either with or without the aid of ethylenediame and/or glycerin, the aqueous solution is mixed with the oil phase containing the lecithin granuals dissolved in the oily organic cosmetically acceptable solvent. These two solutions should be mixed while the aminophylline is maintained in solution. Therefore, it is best to do this mixing immediately after the aminophylline is solubilized in the aqueous solution so that no aminophylline separates from this solution. The step of mixing the oily solution with the water solution should be done immediately after the formation of the water solution with aminophylline. This is true since aminophylline will not remain dissolved in the aqueous solution for very long. When these two solutions are mixed, the resulting solution increases the viscosity and thickness. In this manner, the aminophylline is prevented from separating from the composition, and thus the aminophylline has been effectively "seized up" into the composition. In addition, the oil phase can contain conventional anti-oxidants, preservatives, coloring agents and fragrances. These conventional excipients should be present in the oily phase before it is mixed with the aqueous phase containing aminophylline.

If desired, ethanol can be slowly added to the resulting emulsion, and mixed therewith to provide smoothness and flowabililty of the liquid topical composition. Additionally, the use of ethanol lowers the viscosity of the resulting mixture.

A standard analysis may be used to determine if the composition passes certain quality standards before being provided to consumers. For example, certain tests, specifications, results and test methods may be adhered to in order to determine the quality of the product. For example, appearance of the product may be examined. The specification may require that the final composition have a certain brown opaque coloring. This result may be determined by a visual inspection or automated optical inspections of the product.

An odor or fragrance test may also be used to determine if the product has the proper scent. For example, the specification may require that the product have a cucumber fragrance. A result of the test may be determined by performing an olfactory examination. A pH test may also be conducted. For example, the specification may require that the pH level of the product be within the range of 7.0–7.50. Testing methods to determine the result may be performed with a pH meter 72.

Similarly, a specific gravity test may be performed to determine if a result falls within the bounds of a specification using such methods such as with a pyncometer or specific gravity bottle. Similarly, a viscosity test may be performed on the product to verify that it falls within an acceptable viscosity range.

Likewise, a microbiology test may be used to determine if any microbes grow when the product is added to a medium. In certain embodiments, the results may be determined by performing an aerobic plate count.

From the above discussion, it will be appreciated that the present invention provides emulsion medium wherein aminophylline may be dissolved and transported transdermally, while preventing it from separating after it has been dissolved. In addition, it will also be appreciated that the present invention provides the aminophylline emulsion at a viscosity dispensable in common tubes or pumps for public use while remaining shelf-stable.

The present invention may be embodied in other specific forms without departing from its spirit or essential characteristics. The described embodiments are to be considered in all respects only as illustrative and not restrictive.

EXAMPLE 1

A free flowing gel was prepared with the following ingredients:

Active Ingredient:

| % w/w PER FORMULA | |
|---|---|
| | ACTIVE INGREDIENTS |
| 1.5 | Aminophylline |
| | Other Ingredients: |
| 33.00 | Lecithin |
| 30. | Water |
| 17.00 | Octyl Palmitate |
| 8.2 | Ethyl Alcohol |
| 8.2 | Glycerin |
| 0.80 | Carmel Color |
| 0.64 | Fragrance |
| 0.25 | Ethylenediamine |
| 0.10 | Tocopheryl Acetate |
| 0.075 | Carbomer |
| 0.04 | Propylene Glycol |
| 0.04 | BHA |
| 0.04 | Propyl Gallate |
| 0.04 | Citric Acid |
| 0.075 | DMDM Hydantoin, iodopropynylbutylcarbamate |

The above formulation is prepared utilizing the following procedure. In the following table, the amounts are in grams and are based upon a 1,000 gram gel product.

| | | | Gram |
|---|---|---|---|
| | PHASE I | | |
| A | Octyl Palmitate | | 170 |
| B | Lecithin Granules | | 330 |
| | PHASE II | | |
| C | Fragrance - Cucumber | | 6.4 |
| D | Tocopheryl Acetate (Vit E) | | 1.00 |
| E | Propylene Glycol, BHA, Propyl Gallate, Citric Acid | | 1.6 |
| F | Carmel Color | | 8.0 |
| | PHASE III | | |
| G | Deionized Water | | 300 |
| H | Carbomer 940 | | 0.75 |
| I | Glycerin | | 82.0 |
| J | DMDM Hydantoin, iodopropynylbutylcarbamate (G) | | 0.75 |
| | PHASE IV | | |
| K | Aminophylline | | 15.00 |
| L | Ethylenediamine | | 2.5 |
| | PHASE V | | |
| M | Ethanol | | 82.0 |

Process Instructions:

Step I. Charge main vessel with (A) Octyl Palmitate.

Step II. Turn on sweep and begin adding (B) Lecithin with moderate agitation incrementally to allow turnover of product.

Step III. When mixture is homogenous, add Phase II (C,D,E,F) with continued agitation.

Step IV. While main batch is mixing, to secondary vessel add (G) Water. To the water slowly sprinkle (H) carbomer with moderate agitation and continue mixing until carbomer is thoroughly hydrated. Add (I) Glycerin, and (J).

Step V. Add Phase IV (K) Aminophylline and (L) Ethylenediamine to Phase III and mix until clear. Immediately thereafter add Phase III via slow addition to main batch. Adjust blade speed to continue turnover of main batch.

Step VI. After Phase III has been added, add Phase V (M) Ethanol slowly to main batch and continue mixing until entire batch is smooth and homogenous.

| TEST | SPECIFICATIONS | RESULTS | TEST METHODS |
|---|---|---|---|
| Appearance | Brown Opaque | Brown Opaque | Visual |
| Odor | Cucumber Fragrance | Cucumber Fragrance | Olfactory Examination |
| PH | 7.0–7.5 | 7.32 | pH meter @ 25° C. |
| Specific Gravity | 0.99–1.02 | 1.005 | Bottle Method |
| Viscosity | 75,000–100,000 | 95,310 | Brookfield LVDVE 1Plus |
| Microbiology | Less Than 10 | Less than 10 | Aerobic Plate Count |

EXAMPLE 2

Paste was prepared as follows:

| % w/w PER FORMULA | |
|---|---|
| | ACTIVE INGREDIENTS |
| 1.7 | Aminophylline |
| | Other Ingredients: |
| 36 | Lecithin |
| qs | Water |
| 17 | Octyl Palmitate |
| 8.4 | Glycerin |
| 0.80 | Carmel Color |
| 0.75 | Fragrance |
| 0.25 | Ethylenediamine |
| 0.10 | Tocopheryl Acetate |
| 0.075 | Carbomer |
| 0.04 | Propylene Glycol |
| 0.04 | BHA |
| 0.04 | Propyl Gallate |
| 0.04 | Citric Acid |
| 0.075 | DMDM Hydantoin, iodopropynylbutylcarbamate |

The above formulation is prepared utilizing the following procedure. In the following table, the amounts are in grams and are based upon a 1,000 gram gel product.

| | | Gram |
|---|---|---|
| | PHASE I | |
| A | Octyl Palmitate | 170.00 |
| B | Lecithin Granules | 360.00 |
| | PHASE II | |
| C | Fragrance - Belmay Cucumber | 7.5 |
| D | Tocopheryl Acetate (Vit E) | 1.00 |
| E | Propylene Glycol, BHA, Propyl Gallate, Citric Acid | 1.6 |

-continued

| | | Gram |
|---|---|---|
| F | Carmel Color | 8.0 |
| | PHASE III | |
| G | Deionized Water | 347 |
| H | Carbomer 940 | 0.75 |
| I | Glycerin | 85.0 |
| J | DMDM Hydantoin, iodopropynyl butylcarbamate | 0.75 |
| | PHASE IV | |
| K | Aminophylline | 17.00 |
| L | Ethylenediamine | 2.5 |

Process Instructions:

Step I. Charge main vessel with (A) Octyl Palmitate.

Step II. Turn on sweep and begin adding (B) Lecithin with moderate agitation incrementally to allow turnover of product.

Step III. When mixture is homogenous, add Phase II (C,D,E,F) with continued agitation.

Step IV. While main batch is mixing, to secondary vessel add (G) Water. To the water slowly sprinkle (H) carbomer with moderate agitation and continue mixing until carbomer is thoroughly hydrated. Add (I) Glycerin, and (J).

Step V. Add Phase IV (K) Aminophylline and (L) Ethylenediamine to Phase III and mix until clear. Immediately thereafter add Phase III via slow addition to main batch. Adjust blade speed to continue turnover of main batch. After Phase III has been added continue mixing until entire batch is smooth and homogenous.

EXAMPLE 3

A typical formula for a stabilized aminophylline serum having a concentration of 1.5% aminophylline is:

| Ingredient | Amount per Liter |
|---|---|
| Aminophylline USP | 15.00 g |
| Ethylenediamine | 2.50 g |
| Carbomer - Carbopol 940 ™ | 0.75 g |
| Octyl Palmitate | 258.95 g |
| Lecithin | 502.68 g |
| Fragrance | q.s. |
| Polysorbate 80 | q.s. |
| Steareth-20 | q.s. |
| Poloxamer 401 | q.s. |
| DMDM Hydantoin (and) Iodopropynyl Butylcarbamate - Glydant Plus ™ | q.s. |
| Ethanol | Sufficient for viscosity adjustment |
| Water | q.s. 1000 mL |

The solution is prepared in a glass-lined or stainless steel tank. The lecithin is added to octyl palmitate with agitation until solubilized. This solution is held until clear and free of air.

Polysorbate 80, Steareth-20 and Poloxamer 401 are mixed in a separate vessel and heated to 50–60° C. with agitation. This premix is added to the octyl palmitate with moderate agitation.

In a similar secondary vessel, carbomer is completely hydrolyzed with water. DMDM hydantoin (and) Iodopropynyl Butylcarbamate and Aminophylline, respectively, are solubilized in the water solution sequentially. Ethylenediamine is added to the water solution. The water solution is immediately slowly added to the octyl palmitate solution with continued agitation. Fragrance and ethanol are added to the batch.

EXAMPLE 4

A typical formula for a stabilized aminophylline lotion having a concentration of 1.5% aminophylline is:

| Ingredient | Amount per Liter |
|---|---|
| Aminophylline USP | 15.00 g |
| Ethylenediamine | 2.50 g |
| Carbomer - Carbopol 940 ™ | 0.75 g |
| Octyl Palmitate | 185.1 g |
| Lecithin | 100.0 g |
| Fragrance | q.s. |
| DMDM Hydantoin (and) Iodopropynyl Butylcarbamate - Glydant Plus ™ | q.s. |
| Ethanol | Sufficient for viscosity adjustment |
| Water | q.s. 1000 mL |

The solution is prepared in a glass-lined or stainless steel tank. The lecithin is added to octyl palmitate with agitation until solubilized. This solution is held until clear and free of air.

In a similar secondary vessel, carbomer is completely hydrolyzed with water. DMDM hydantoin (and) Iodopropynyl Butylcarbamate and Aminophylline, respectively are solubilized in the water solution sequentially. Ethylenediamine is added to the water solution. The water solution is immediately added to the octyl palmitate with high agitation. Fragrance and ethanol are added to the batch.

What is claimed is:

1. A water in oil emulsion of stabilized aminophylline for transdermal delivery of aminophylline to reduce cellulite, comprising:
   a water phase containing an effective amount of aminophylline for transdermal delivery to reduce cellulite, said water phase comprising discrete micelles of aminophylline bound by a pseudoplastic or thixotropic agent for maintaining the amino phylline in solution in the water phase; and
   an oil phase in which said water phase is dispersed, said oil phase containing lecithin dissolved in a cosmetically acceptable water insoluble organic oil;
   whereby said lecithin serves as a carrier for the aminophylline to stabilize the aminophylline in solution for transdermal delivery.

2. The water in oil emulsion of claim 1 wherein said emulsion is in the form of a gel, lotion, ointment, paste, cream or serum.

3. The composition of claim 1 wherein said pseudoplastic agent is a carbomer.

4. The composition of claim 3 wherein said water phase contains glycerin in addition to said carbomer.

5. The composition of claim 4 wherein said oil which forms the oil phase is octyl palmitate.

6. The composition of claim 5 wherein the aqueous phase contains ethylenediamine.

7. The composition of claim 6 wherein said composition is in the form of a gel.

8. The composition of claim 1 wherein the water phase micelles are homogeneously dispersed in the oil phase.

9. A composition for transdermal delivery of aminophylline, comprising an aqueous phase disbursed as discreet micelles in a continuous oil phase, said aqueous phase containing from about 0.1% to about 5% by weight, based upon the weight of the composition, of aminophylline bound by a pseudoplastic or thixotropic agent for maintaining the aminophylline in solution, said oil phase containing lecithin, dissolved in a water insoluble cosmetically acceptable organic oil, as a carrier for stabilizing the aminophylline in the aqueous phase for transdermal delivery of the aminophylline.

10. The composition of claim 9 wherein the water phase micelles are homogeneously dispersed in the oil phase.

11. The composition of claim 10 when said pseudoplastic agent is a carbomer which is present in an amount of 0.003% to 2.00% by weight of the composition.

12. The composition of claim 11 wherein lecithin is present in the oil phase in an amount from about 2% to 80% by weight based upon the weight of the composition.

13. The composition of claim 12 wherein the oil which constitutes the oil phase is octyl palmitate.

14. The composition of claim 13 when the aqueous phase includes ethylenediamine in an amount from about 0.001% to 2.5% by weight.

15. The composition of claim 14 wherein the aqueous phase contains glycerin.

16. The composition of claim 15 wherein the composition contains ethanol in an amount sufficient to provide the composition as a free flowing gel.

17. A process for preparing a water in oil emulsion for transdermal delivery of aminophylline, comprising:
   a. providing a first, oil-based solution of lecithin dissolved in a water-insoluble organic oil to act as a carrier for aminophylline;
   b. preparing a second, aqueous solution by dissolving a pseudoplastic or thixotropic agent in aqueous medium followed by dissolving aminophylline in said aqueous medium in which said pseudoplastic or thixotropic agent was dissolved to bind the aminophylline to said pseudoplastic or thixotropic agent to stabilize the aminophylline in the aqueous solution; and
   c. mixing said first solution with said second solution while said aminophylline remains dissolved in said second solution, and thereby forming said water in oil emulsion with said aminophylline being stabilized within the water phase by being bound by said lecithin in said oil solution.

18. The process of claim 17 wherein said agent in said second solution is carbomer.

19. The method of claim 18 wherein in preparing the second solution glycerin is dissolved in said aqueous medium prior to dissolving aminophylline in the solution.

20. The process of claim 19 wherein the first and second solution are mixed under agitation.

21. The process of claim 20 wherein ethanol is added after forming said emulsion.

22. The process of claim 19 wherein ethylenediamine is dissolved in the second solution together with aminophylline.

* * * * *